United States Patent [19]

Matsuura et al.

[11] Patent Number: 6,089,857

[45] Date of Patent: Jul. 18, 2000

[54] HEATER FOR GENERATING FLAVOR AND FLAVOR GENERATION APPLIANCE

[75] Inventors: Sadayoshi Matsuura; Manabu Takeuchi, both of Tokyo, Japan

[73] Assignee: Japan Tobacco, Inc., Tokyo, Japan

[21] Appl. No.: 09/011,972

[22] PCT Filed: Jun. 9, 1996

[86] PCT No.: PCT/JP97/01954

§ 371 Date: Feb. 20, 1998

§ 102(e) Date: Feb. 20, 1998

[87] PCT Pub. No.: WO97/48294

PCT Pub. Date: Dec. 24, 1997

[30] Foreign Application Priority Data

Jun. 21, 1996 [JP] Japan ................................. 8-161927

[51] Int. Cl.[7] .................................................. F23Q 2/00
[52] U.S. Cl. .................... 431/142; 431/153; 431/144; 131/329
[58] Field of Search .................... 431/142, 144, 431/143, 153; 131/329

[56] References Cited

U.S. PATENT DOCUMENTS

| | | | |
|---|---|---|---|
| 1,535,934 | 4/1925 | McFadden | 131/174 |
| 3,397,703 | 8/1968 | Otto | 131/201 |
| 4,474,191 | 10/1984 | Steiner | 131/198.2 |
| 4,846,199 | 7/1989 | Rose | 131/329 |
| 4,922,901 | 5/1990 | Brooks et al. | 128/203.26 |
| 4,945,928 | 8/1990 | Rose | 131/270 |
| 4,945,931 | 8/1990 | Gori | 131/335 |
| 4,947,874 | 8/1990 | Brooks et al. | 131/329 |
| 4,947,875 | 8/1990 | Brooks et al. | 131/330 |
| 5,316,759 | 5/1994 | Rose et al. | 514/343 |
| 5,613,504 | 3/1997 | Collins et al. | 131/94 |
| 5,848,596 | 12/1998 | Zelenik | 131/329 |

FOREIGN PATENT DOCUMENTS

| | | |
|---|---|---|
| 358002A2 | 8/1989 | European Pat. Off. . |
| 358114A2 | 8/1989 | European Pat. Off. . |
| 2-124081 | 5/1990 | Japan . |
| 2-124082 | 5/1990 | Japan . |
| 3-232481 | 10/1991 | Japan . |

*Primary Examiner*—Larry Jones
*Attorney, Agent, or Firm*—Birch, Stewart, Kolasch & Birch, LLP

[57] ABSTRACT

A flavor generation piece (12) incorporates a formed body (32) of a material containing a flavor substance. A heater (42) heats the flavor generation piece (12) without burning it, thereby generating a flavor. The heater (42) has a tank (46) mounted in a heat-insulating holder (44) to store a combustible gas. A combustion portion (52) for burning the combustible gas is disposed on the tank (46). Ignition or extinction of the combustion portion (52) is selected by a switch (58). The upper portion of the heat-insulating holder (44) forms a heat exchange duct (62) surrounding the combustion portion (52) and providing an exhaust path (64). An air pipe (74) is disposed to cross the heat exchange duct (62) transversely in the exhaust path (64). Heat exchange is performed between a fluid flowing in the exhaust path (64) and a fluid flowing in the air pipe (74). A socket (76) communicating with the air pipe (74) to detachably mount the flavor generation piece (12) is disposed on the outer side surface of the heat-insulating holder (44).

3 Claims, 3 Drawing Sheets

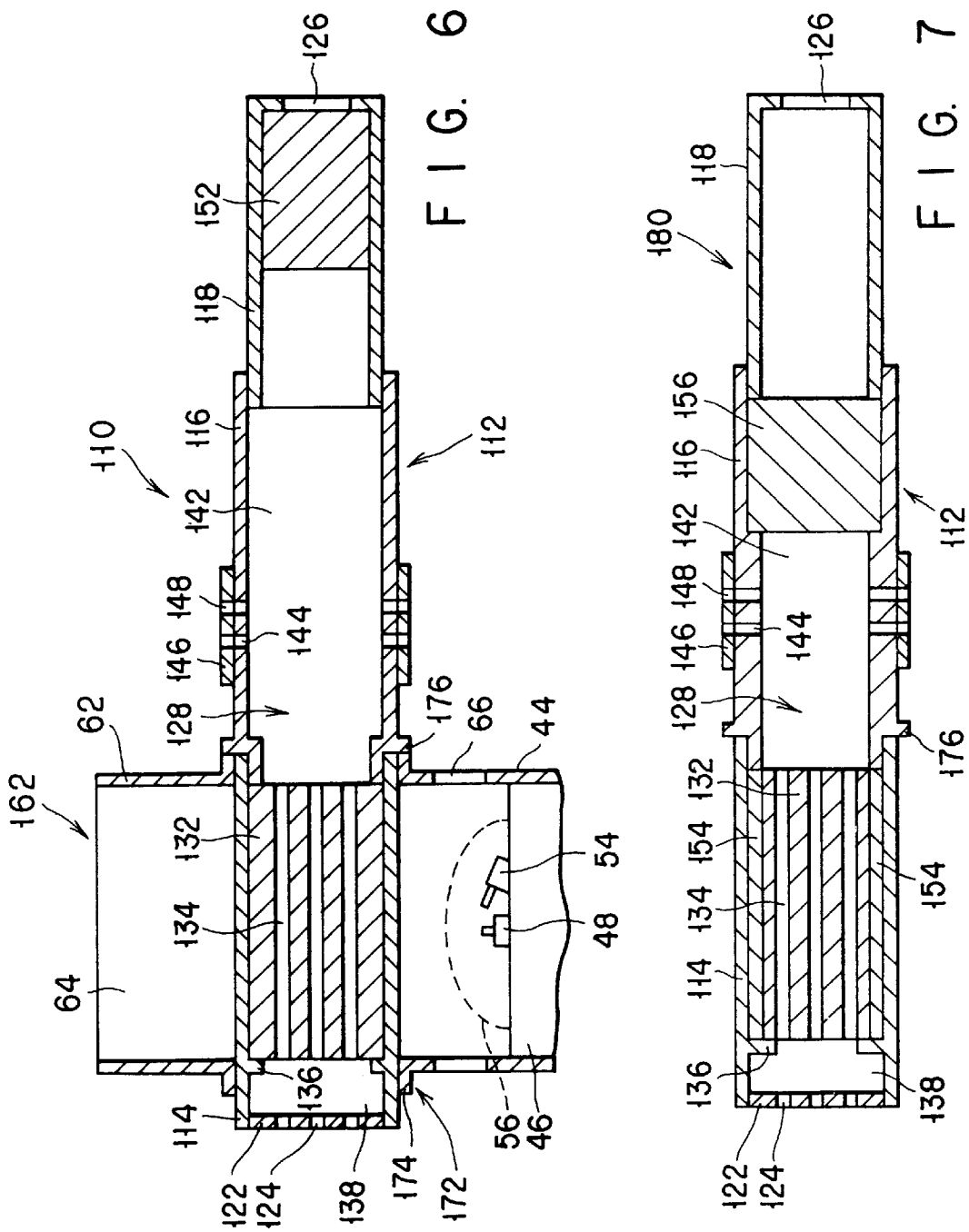

ies have been proposed.
HEATER FOR GENERATING FLAVOR AND FLAVOR GENERATION APPLIANCE This application is the national phase under 35 U.S.C. §371 of prior PCT International Application No., PCT/JP97/01954, which has an International filing date of Jun. 9, 1996, which designated the United States of America, the entire contents of which are hereby incorporated by reference.

TECHNICAL FIELD

The present invention relates to a heater for heating a flavor generation piece in order to enjoy inhalation of a flavor and simulated smoking and a flavor generation instrument using the same and, more particularly, to a flavor generation heater and instrument used for generating a flavor as an inhalation target by heating a material and not by combustion.

BACKGROUND ART

A simulated smoking article employed for enjoying the flavor and smoke of tobacco without burning tobacco is already known, and various types of simulated smoking articles have been proposed.

Jpn. Pat. Appln. KOKAI Publication No. 3-232481 discloses a typical concept of a conventional simulated smoking article. The article of this reference uses, e.g., a rod-like solid material. When the solid material is heated by an electric heating element, an inhalation target, e.g., a flavor, is generated.

In the article utilizing such an electric heating element, if a power supply is incorporated in the article, the internal structure is complicated to increase the cost, and once the article causes a trouble, it is difficult to repair. In use of an external power supply, if the power supply and the smoking article are connected to each other with a cord, not only the location where the article can be used is limited, but also the cord becomes an obstacle. Inversely, if the article is formed such that it is removed from the external power supply when used for smoking, the heated state of the material can only be maintained until the user's inhalation (puffing) operation is complete about once or twice.

U.S. Pat. No. 4,945,931 discloses a simulated smoking article using a pressurized aerosol container. In the article of this reference, the puffing operation of the user swings the vanes to mechanically open the outlet port of the container, and the aerosol is emitted.

In the article utilizing such a pressurized flavor gas source, it is difficult to adjust the opening/closing valve such that the flavor gas can be emitted continuously. More specifically, in the article of this type, if the opening/closing vale is formed to have a simple structure, all of the pressurized flavor gas may undesirably be emitted until a puffing operation is complete twice or three times.

DISCLOSURE OF INVENTION

The present invention has been made in view of the above problems, and has as its object to provide a flavor generation heater and instrument which have a simple structure and enable continuous generation of a flavor.

According to the first aspect of the present invention, there is provided a heater for heating, without burning, a flavor generation piece, having an air intake port for taking in air therein and a suction port through which a user inhales a flavor and incorporating a material containing at least a flavor substance, thereby generating the flavor, characterized by comprising:

a tank for storing a combustible gas;

a combustion portion for burning the combustible gas;

a switch for performing a selecting operation between ignition and extinction of the combustion portion;

a heat exchange duct surrounding the combustion portion and forming an exhaust path;

an air pipe crossing the heat exchange duct transversely in the exhaust path, heat exchange being performed between a fluid flowing in the exhaust path and a fluid flowing in the air pipe; and a socket communicating with the air pipe to detachably mount the flavor generation piece.

According to the second aspect of the present invention, there is provided a heater for heating, from an outside of a heat conduction wall without burning, a material which is stored inside the heat conduction wall of a flavor generation piece and contains at least a flavor substance, thereby generating a flavor, the flavor generation piece having an air intake port for taking in air therein and a suction port through which a user inhales the flavor, characterized by comprising:

a tank for storing a combustible gas;

a combustion portion for burning the combustible gas;

a switch for performing a selecting operation between ignition and extinction of the combustion portion;

a heat exchange duct surrounding the combustion portion and forming an exhaust path; and an opening support formed on the heat exchange duct to detachably mount the flavor generation piece such that the heat conduction wall is located in the exhaust path.

According to the third aspect of the present invention, there is provided a flavor generation instrument characterized by comprising:

a tank for storing a combustible gas;

a combustion portion for burning the combustible gas;

a switch for performing a selecting operation between ignition and extinction of the combustion portion;

a heat exchange duct surrounding the combustion portion and forming an exhaust path;

an air pipe crossing the heat exchange duct transversely in the exhaust path, heat exchange being performed between a fluid flowing in the exhaust path and a fluid flowing in the air pipe;

a socket communicating with the air pipe; and a flavor generation piece detachably mounted in the socket, the flavor generation piece having an air intake port for taking in air therein and a suction port through which a user inhales a flavor and incorporating a material containing at least a flavor substance, and the material being heated, without being burned, with heat from the combustion portion, thereby generating the flavor.

According to the present invention, there is provided a simple flavor generation heater and instrument that enable generation of the flavor by continuously heating a flavor generation piece incorporating a material containing a flavor substance.

BRIEF DESCRIPTION OF DRAWINGS

FIG. 6 is a longitudinal sectional side view showing a flavor generation instrument according to another embodiment of the present invention, in which a flavor generation piece is mounted in a flavor generation heater; and FIG. 7 is a longitudinal sectional side view showing a modification of the flavor generation piece that can be used in the flavor generation piece shown in FIG. 6.

BEST MODE OF CARRYING OUT THE INVENTION

Figure 1:
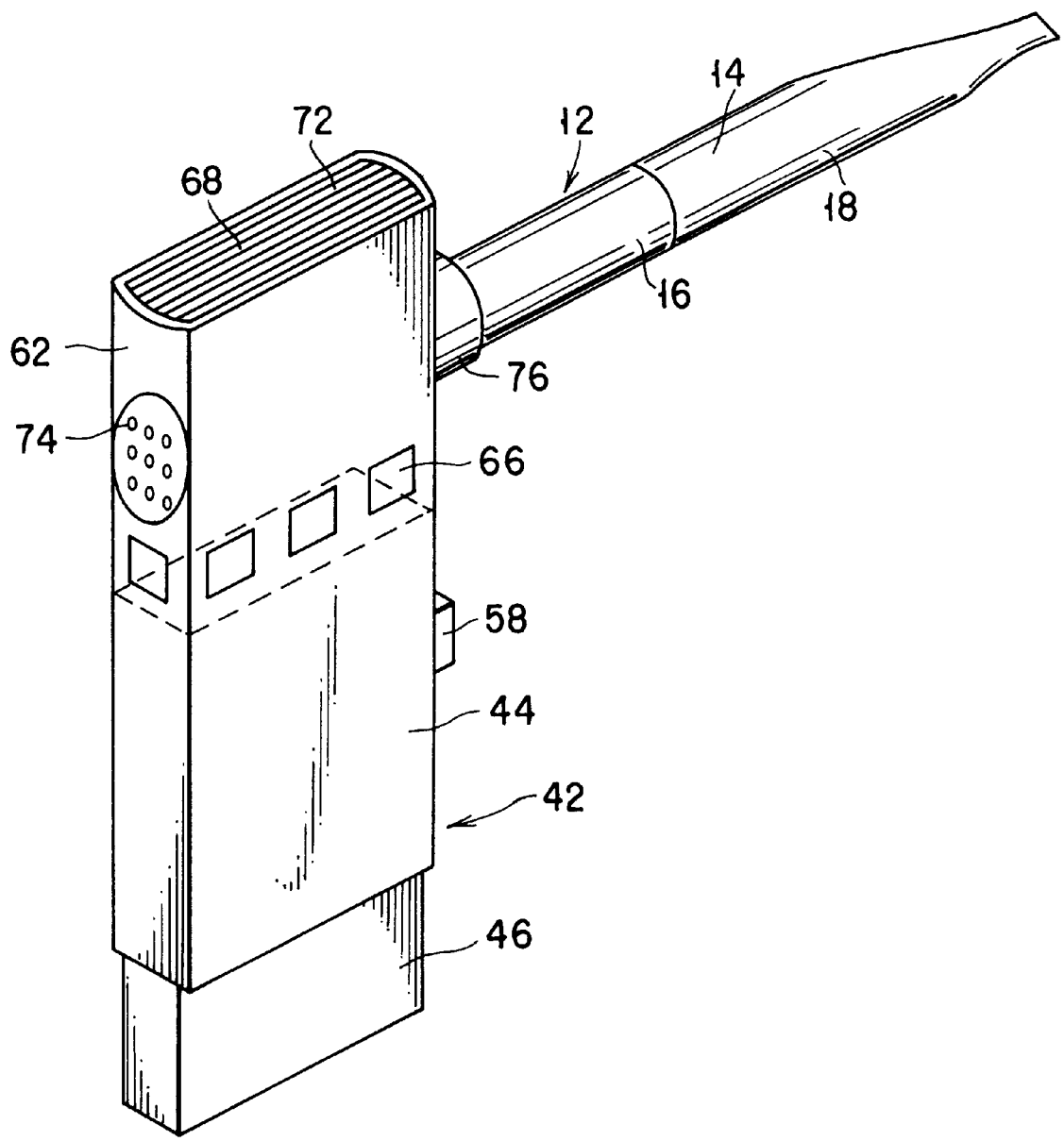
FIG. 1 is a perspective view showing a flavor generation instrument according to an embodiment of the present invention, in which a flavor generation piece is mounted in a flavor generation heater.

FIG. 1 is a perspective view showing a flavor generation instrument according to an embodiment of the present invention, in which a flavor generation piece is mounted in a flavor generation heater.

Figure 4:
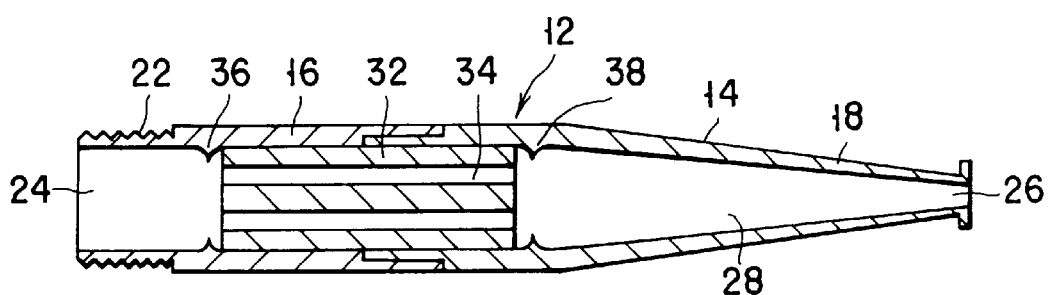
FIG. 4 is a longitudinal sectional side view showing the flavor generation piece shown in FIG. 1.

As shown in FIG. 4, a flavor generation piece 12 has a cylindrical pipe casing 14 having such an outer diameter that the user can hold the pipe casing 14 in his mouth. The casing 14 has a heat-insulating tube 16 and a mouthpiece 18 each made of a heat-resistant heat-insulating material, e.g., a synthetic resin. These members 16 and 18 are detachably connected to each other with a known connection structure, e.g., screws or a fitting pair.

A male thread 22 for mounting the flavor generation piece 12 in a heater 42 (to be described later) is formed on the end portion of the heat-insulating tube 16. In correspondence to this, the end face of the heat-insulating tube 16 is open, and an air intake port 24 for taking in air into the casing 14 is formed in the end face of the heat-insulating tube 16. The end face of the mouthpiece 18 is also open, and a suction port 26 through which the user inhales the flavor is formed in the end face of the mouthpiece 18. The mouthpiece 18 is tapered such that its diameter decreases toward the suction port 26. A gas flow path 28 is defined in the casing 14 between the air intake port 24 and the suction port 26.

A formed body 32 of a solid material for generating the flavor or the like to be inhaled by the user is detachably stored in the casing 14. The formed body 32 is positioned to be sandwiched between projections 36 and 38 formed on the inner surfaces of the heat-insulating tube 16 and mouthpiece 18, respectively.

The formed body 32 of the material can contain an extracted material and/or the constituent components of various types of natural materials in accordance with the application purpose. As the flavor substance to be contained by the formed body 32, for example, menthol, caffeine, a precursor, e.g., glycoside, that generates a flavor upon thermal decomposition, or a tobacco component, e.g., a tobacco extracted component or a tobacco smoke condensate component can be employed. In order to add smoke to the flavor, the formed body 32 can contain a substance which generates aerosol when heated. As the substance that generates aerosol, polyols, e.g., glycerin or propylene glycol, lower alcohols, saccharide, or their mixtures can be used. The formed body 32 can contain a gas adsorbent, e.g., activated carbon, silica gel, or activated alumina.

The formed body 32 is formed as a dense cylinder having a low air permeability, and has such a size that no gap is formed between its outer surface and the inner surface of the casing 14. Accordingly, a plurality of through holes 34 are formed in the formed body 32 in the axial direction, and the gas flow path 28 between the air intake port 24 and suction port 26 is formed through the through holes 34.

The formed body 32 can be formed to such a size that a gap is formed between its outer surface and the inner surface of a heat conduction tube 14. The formed body 32 need not be made of a dense material having no air permeability but can be made of a material having a high permeability, e.g., an unwoven fabric bundle made of activated carbon fibers, natural cellulose fibers, or cellulose derivative fibers. In such a case, no through holes 34 need be formed.

The heater 42 is used to generate the flavor by heating the flavor generation piece 12 without burning it. The heater 42 has a heat-insulating holder 44 made of a heat-resistant heat-insulating material, e.g., a synthetic resin, and a rectangular tank 46 detachably attached under the holder 44 to store combustible gas.

Figure 2:
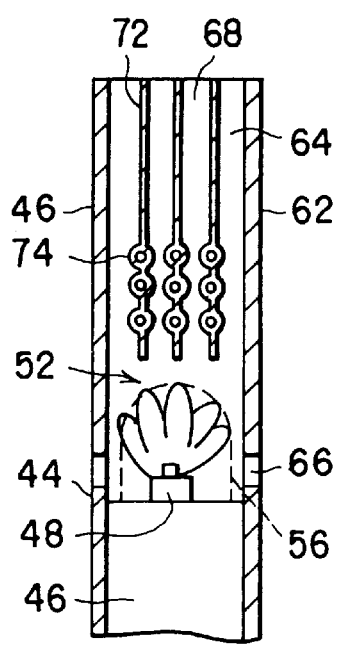
FIG. 2 is a partial longitudinal sectional side view showing a flavor generation heater shown in FIG. 1.
Figure 3:
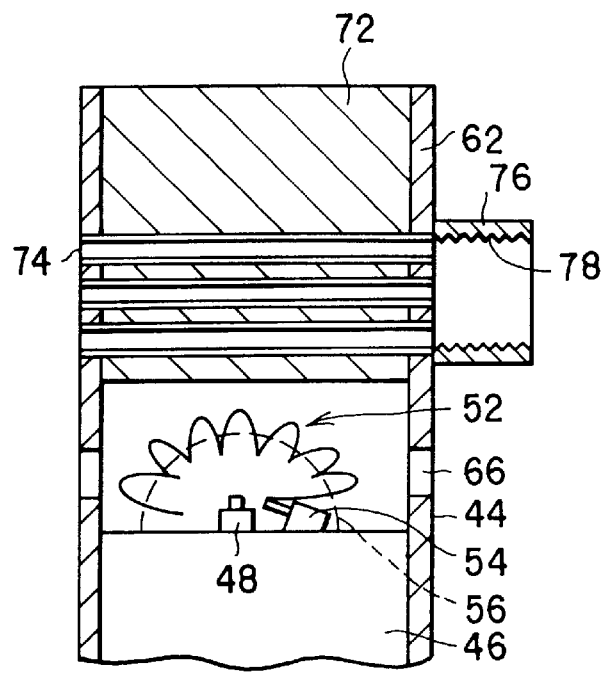
FIG. 3 is a partial longitudinal sectional front view showing the flavor generation heater shown in FIG. 1.

As shown in FIGS. 2 and 3, a gas nozzle 48 is disposed on the tank 46, and a combustion portion 52 for burning the combustible gas is formed on the gas nozzle 48. A sparking plug 54 is disposed in the combustion portion 52 to oppose the gas nozzle 48. The gas nozzle 48 and sparking plug 54 are covered with a dome-like metal mesh member 56. The selecting operation between ignition and extinction of the combustion portion 52 is performed by a switch 58 disposed on the side surface of the lower portion of the holder 44. It is also possible to perform a control operation such that the combustion portion 52 performs automatic extinction after it performs combustion for a predetermined period of time upon turning on the switch 58.

The upper portion of the holder 44 forms a heat exchange duct 62 that surrounds the combustion portion 52 and provides an exhaust path 64 for exhaust combustible gas generated by the combustion portion 52. A plurality of air inlet openings 66 are formed in the entire portion of the side wall of the heat exchange duct 62 around the combustion portion 46. The top portion of the heat exchange duct 62 is open to form an exhaust port 68 that emits exhaust combustible gas generated by the combustion portion 46.

A plurality of heat exchange fins 72 for performing heat exchange with the exhaust combustible gas are disposed in the exhaust path 64 between the combustion portion 52 and exhaust port 68. Each fin 72 is formed with a plurality of air pipes 74 that extend through the heat exchange duct 62 transversely. One end portion of each air pipe 74 is open at one outer side surface of the heat exchange duct 62, and the other end portion thereof is open at the other outer side surface of the heat exchange duct 62. The air pipes 74 extend through the heat exchange duct 62 in a sealed state so that the fluid in the exhaust path 64, i.e., the exhaust combustible gas, will not flow into them. Accordingly, heat exchange between the fluid flowing through the air pipes 74, i.e., air, and the exhaust combustible gas flowing in the exhaust path 64 is performed through the fins 72 and air pipes 74. Air flowing in the air pipes 74 is set to be heated to a temperature equal to or higher than 50° C., at which flavor generation is possible, and preferably equal to or higher than 180° C.

A socket 76 is provided to the outer side surface of the heat exchange duct 62 to communicate with the air pipes 74. A female thread 78 to threadably engage with the male thread 22 of the flavor generation piece 12 is formed in the socket 76. The flavor generation piece 12 can be detachably mounted on the heater 42 through engagement of the threads 22 and 78.

Figure 5:
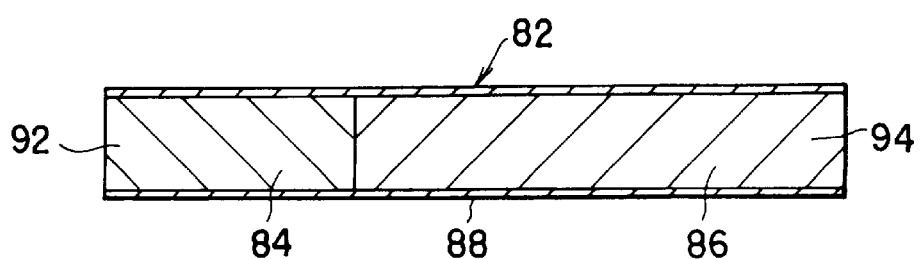
FIG. 5 is a longitudinal sectional side view showing a modification of the flavor generation piece that can be used in the flavor generation heater shown in FIG. 1.

In the heater 42 shown in FIGS. 1 to 3, a flavor generation piece 82 shown in FIG. 5 may be mounted instead. In the flavor generation piece 82, a material bundle 84 as an unwoven fabric bundle of a material that generates the flavor or the like to be inhaled by the user and having a high air permeability, and a filter 86 having poor filtration properties are connected to each other with paper 88. The end face of the material bundle 84 forms an air intake port 92 for taking in air into the flavor generation piece 82, and the end face of the filter 86 forms a suction port 94 through which the user inhales the flavor. Accordingly, when the end portion of the flavor generation piece 82 on the material bundle 84 side is inserted in the socket 76, the flavor generation piece 82 can be used for inhalation of flavor, in the same manner as the flavor generation piece 12 shown in FIG. 4.

The filter 86 can be made of a normal tobacco filter material made of cellulose acetate, pulp, or the like. The filter 86 can contain a gas adsorbent, e.g., activated carbon, silica gel, or activated alumina.

FIG. 6 is a longitudinal sectional side view showing a flavor generation instrument according to another embodiment of the present invention, in which a flavor generation piece is mounted in a flavor generation heater.

A flavor generation piece 110 according to this embodiment has a cylindrical pipe casing 112 having such an outer diameter that the user can hold the casing 112 in his mouth. The casing 112 has a heat conduction tube 114 made of a heat-resistant heat-conductive material, e.g., a metal or a ceramic material, and a heat-insulating tube 116 and a mouthpiece 118 each made of a heat-resistant heat-insulating material, e.g., a synthetic resin. These members 114, 116, and 118 are detachably connected to each other with known connection structures, e.g., screws or fitting pairs.

An end plate 122 made of a heat-resistant material, e.g., a metal or a ceramic material, is disposed on the end face of the heat conduction tube 114. A plurality of air intake ports 124 for taking in air into the casing 112 are formed in the end plate 122. In correspondence to this, a suction port 126 through which the user inhales the flavor is formed in the end portion of the mouthpiece 118. A gas flow path 128 is defined in the casing 112 between the air intake ports 124 and the suction port 126.

A formed body 132 of a solid material for generating a flavor or the like to be inhaled by the user is detachably stored in the heat conduction tube 114. The formed body 132 is formed as a dense cylinder having a low air permeability, and has such a size that no gap is formed between its outer surface and the inner surface of the heat conduction tube 114. Accordingly, a plurality of through holes 134 are formed in the formed body 132 in the axial direction, and the gas flow path 128 between the air intake ports 124 and suction port 126 is formed through the through holes 134. The formed body 132 can be made of the same material as that of the formed body 32 of the flavor generation piece 12 shown in FIG. 4.

The formed body 132 is positioned to be sandwiched between a projection 136, formed on the inner surface of the heat conduction tube 114, and the end portion of the heat-insulating tube 116 connected to the heat conduction tube 114. Therefore, a space that serves as a manifold head 138 of taken air is formed between the formed body 132 and the end plate 122 of the heat conduction tube 114.

A cooling chamber 142 arranged to partly constitute the gas flow path 128 is formed between the formed body 132 and suction port 126. Outer air inlet holes 144 are formed in the side wall of the heat-insulating tube 116 that defines the cooling chamber. The heated gas containing the flavor generated by the formed body 132 is mixed with outer air and cooled in the cooling chamber 142.

An adjusting ring 146 having a plurality of holes 148 is disposed on the heat-insulating tube 116 around the outer air inlet holes 144. When the position of the adjusting ring 146 is adjusted with respect to the outer air inlet holes 144, the effective rate of the outer air inlet holes 144 is adjusted, thereby changing the amount of flavor contained in the gas or temperature of the gas that reaches the suction port 126.

A filter 152 is disposed in the mouthpiece 118 to cover the suction port 126. When the filter 152 is disposed, the pressure loss can be adjusted so that the gas can be inhaled with an appropriate pressure. The filter 152 can be made of a normal tobacco filter material made of cellulose acetate, pulp, or the like. The filter 152 can contain a gas adsorbent, e.g., activated carbon, silica gel, or activated alumina.

In a heater 162 of the embodiment shown in FIG. 6, only the structure of its heat exchange duct 62 is slightly different from that of the heater 42 shown in FIGS. 1 to 3. Accordingly, portions of the heater 162 that are common to the heater 42 are denoted by the same reference numerals, and a detailed description thereof will be omitted.

No fins corresponding to the heat exchange fins 72 or no air pipes corresponding to the air pipes 74 shown in FIGS. 1 to 3 are formed in a heat exchange duct 62 in the upper portion of a heating holder 44. Instead, a pair of opening supports 172 for allowing the heat conduction tube 114 to be detachably inserted in a tight contact state are formed on the opposing side walls of the heat exchange duct 62. Each opening support 172 has an opening formed in the side wall and a support ring 174 projecting from the side wall outward to be aligned with the opening.

The heat conduction tube 114 and the heat exchange duct 62 are positioned relative to each other by abutting a projection 176, formed on the heat-insulating tube 116, against the side surface of one support ring 174 of the heat exchange duct 62. When the heat conduction tube 114 is positioned with respect to the heat exchange duct 62, the heat conduction tube 114 is mounted in the heat exchange duct 62, as shown in FIG. 6, such that it extends through the pair of support rings 174. At this time, the heat conduction tube 114 is located in an exhaust path 64, and the air intake ports 124 of the casing 112 and the heat-insulating tube 116 are located outside the heat exchange duct 62.

In the flavor generation piece 110 and heater 162 shown in FIG. 6, usually, the flavor is inhaled with the casing 112 being mounted in the heat exchange duct 62. However, it is also possible to utilize preheat of the heat conduction tube 114 and inhale the flavor with the casing 112 being removed from the heat exchange duct 62. FIG. 7 is a longitudinal sectional side view showing a flavor generation piece 180 suitable for such a case. In FIG. 7, portions that are common to FIG. 6 are denoted by the same reference numerals as in FIG. 6, and a detailed description thereof will be omitted.

The characteristic feature of the flavor generation piece 180 shown in FIG. 7 primarily resides in that the inner surface of a heat conduction tube 114 is covered with a heat accumulating material layer 154. When the heat accumulating material layer 154 is disposed, the temperature of a formed body 132 in the heat conduction tube 114 can be maintained at a flavor generation temperature for a longer period of time even after the casing 114 is removed from a heater 162.

As the material of the heat reservoir 154, a sensible heat type material utilizing only the specific heat of a substance, e.g., an inorganic compound such as silica gel, alumina, carbons, glass mat, glass fiber, or minerals; or a metal or alloy such as aluminum, iron, silver, or lead can be used. As another heat accumulating material, a material utilizing heat of fusion to increase the quantity of heat, e.g., a compound such as paraffin, sodium acetate, naphthalene, wax, or polyethylene oxide, or a metal or an alloy such as zinc, tin, solder, or soft wax can be used. More specifically, when generating aerosol, it is preferable to use a sensible heat type material; and when generating only flavor, it is preferable to use a material utilizing heat of fusion.

A filler 156 is disposed in a cooling chamber 142. When the filler 156 is disposed, the cooling effect of the gasified flavor component can be promoted, and the pressure loss can be adjusted so that the flavor component can be inhaled with an appropriate pressure. As the filler 156, for example, a fiber formed body made of cellulose acetate or pulp, or a particulate matter, e.g., glass or aluminum particles, can be used.

The characteristic features of the respective portions of the present invention have been described divisionally by way of several embodiments in order to facilitate understanding of the present invention. These characteristic features can be appropriately combined in accordance with purposes. More specifically, the present invention can be practiced in various embodiments other than those shown in the drawings within the spirit and scope of the invention.

We claim:

1. A flavor generation heater for heating, without burning, a flavor generation piece, having an air intake port for taking in air therein and a suction port through which a user inhales a flavor and incorporating a material containing at least a flavor substance, thereby generating the flavor, characterized by comprising:

a tank for storing a combustible gas;

a combustion portion for burning said combustible gas;

a switch for performing a selecting operation between ignition and extinction of said combustion portion;

a heat exchange duct surrounding said combustion portion and forming an exhaust path;

an air pipe crossing said heat exchange duct transversely in said exhaust path, heat exchange being performed between a fluid flowing in said exhaust path and a fluid flowing in said air pipe; and a socket communicating with said air pipe to detachably mount said flavor generation piece.

2. A heater for heating, from an outside of a heat conduction wall without burning, a material which is stored inside said heat conduction wall of a flavor generation piece and contains at least a flavor substance, thereby generating flavor, said flavor generation piece having an air intake port for taking in air therein and a suction port through which a user inhales flavor, characterized by comprising:

a tank for storing a combustible gas;

a combustion portion for burning said combustible gas;

a switch for performing a selecting operation between ignition and extinction of said combustion portion;

a heat exchange duct surrounding said combustion portion and forming an exhaust path; and an opening support formed on said heat exchange duct to detachably mount said flavor generation piece such that said heat conduction wall is located in said exhaust path.

3. A flavor generation instrument characterized by comprising:

a tank for storing a combustible gas;

a combustion portion for burning said combustible gas;

a switch for performing a selecting operation between ignition and extinction of said combustion portion;

a heat exchange duct surrounding said combustion portion and forming an exhaust path;

an air pipe crossing said heat exchange duct transversely in said exhaust path, heat exchange being performed between a fluid flowing in said exhaust path and a fluid flowing in said air pipe;

a socket communicating with said air pipe; and a flavor generation piece detachably mounted in said socket, said flavor generation piece having an air intake port for taking in air therein and a suction port through which a user inhales a flavor and incorporating a material containing at least a flavor substance, and said material being heated, without being burned, with heat from said combustion portion, thereby generating the flavor.

* * * * *

UNITED STATES PATENT AND TRADEMARK OFFICE
CERTIFICATE OF CORRECTION

PATENT NO. : 6,089,857
DATED : July 18, 2000
INVENTOR(S) : Sadayoshi Matsuura et al.

It is certified that error appears in the above-identified patent and that said Letters Patent is hereby corrected as shown below:

Item "[22] PCT Filed:", please change "Jun. 9, 1996" to -- Jun. 9, 1997 --.

<u>Column 1,</u>
Line 6, please change "Jun. 9, 1996" to -- Jun. 9, 1997 --.

Signed and Sealed this

Ninth Day of October, 2001

*Attest:*

NICHOLAS P. GODICI
*Attesting Officer*     *Acting Director of the United States Patent and Trademark Office*